United States Patent [19]

Gutbier

[11] Plant 4,235

[45] Apr. 4, 1978

[54] POINSETTIA PLANT NAMED GUTBIER V-10

[75] Inventor: Gregor Gutbier, Linz, Germany

[73] Assignee: Paul Ecke, Jr., Encinitas, Calif.

[21] Appl. No.: 801,160

[22] Filed: May 27, 1977

[51] Int. Cl.[2] ..... A01H 5/00

[52] U.S. Cl. ..... Plt./68

[58] Field of Search ..... Plt./86

*Primary Examiner*—Robert E. Bagwill

*Attorney, Agent, or Firm*—Chas. W. Rummler

[57] ABSTRACT

A new cultivar of poinsettia plant distinguished by its shorter than average growth habit and its ability to bloom in 8 to 9 weeks at a night temperature in the range of 14° to 16° C. with a prolific production of medium red bracts which have a unique arched appearance. When grown as a branched or pinched plant, this cultivar produces more branches or shoots than any poinsettia heretofore known; and when grown as a single stem plant, it produces a great number of side shoots which greatly enhances its beauty. In general appearance, this new variety is unique and different in many respects from any poinsettia ever before produced.

1 Drawing Figure

BACKGROUND OF THE NEW PLANT

This new variety of poinsettia plant originated as a seedling of unknown parentage resulting from extensive hybridizing efforts carried on by me at Linz (Rhein), Germany, with the object of developing new and improved varieties for the commercial trade. This plant was discovered by me in the course of my study of various greenhouse grown seedlings produced by a multitude of crosses, made by me from time to time, and I selected this particular plant for propagation and test because of its distinctly different appearance and habits.

Propagation of my new poinsettia discovery was done by me, by means of cuttings from the original plant, in my greenhouse at Linz (Rhein), Germany, and propagation of the resulting clone through successive generations has shown that the novel and distinctive characteristics of the original plant hold true from generation to generation and appear to be firmly fixed. Propagation of this new poinsettia plant variety is now being done for the commercial market by means of vegetative cuttings at Encinitas, Calif.

DESCRIPTION OF THE DRAWING

My new variety of poinsettia is illustrated by the accompanying photographic drawing which shows, in full color, flowers, bracts and foliage of the plant in full bloom, the color reproduction being as nearly true as is reasonably possible to obtain by conventional professional photographic procedures.

DESCRIPTION OF THE NEW PLANT

The following is a detailed description of my new variety of poinsettia plant with color designations according to the R.H.S. Colour Chart published by The Royal Horticultural Society of London, England.

THE PLANT

Origin: Seedling.

Parentage: Unknown.

Classification:

*Botanic.*—*Euphorbia pulcherrima.*

*Commercial.*—Greenhouse poinsettia.

Form: Shrub.

Height: Short.

Growth habit:

*As a single stem.*—Upright and vigorous with self-branching side shoots; usually will not require growth regulator.

*As a branched plant.*—Upright with very many stems producing a bushy, full appearance. If grown too warm or too soft, the stems of this plant will not be self-supporting.

Growth rate: Very fast. Rooting occurs in 10 to 15 days under automatic mist and the plant will bloom in 8 to 9 weeks at a night temperature of 14° to 16° C. (57° to 61° F.) during October and November. With poor light conditions, a somewhat higher temperature may be necessary.

Foliage: Alternate, horizontal, with medium persistence and in normal abundance.

*Leaf size.*—Medium. 3 to 6 inches long and 2½ to 4½ inches wide.

*Leaf shape.*—Ovate, with acuminate apex and substantially entire margins, some being undulate and with dentations.

*Aspect.*—Upper side — Smooth and medium glossy. Under side — Dull with ordinary veining.

*Color.*—Upper side — Dark Green, RHS 139A. Under side — Dark Green, RHS 137A.

*Retention.*—The foliage lasts well when kept at a low room temperature, i.e. below 20° C. (68° F.), and with good light intensity. When kept in over-heated and dark rooms, the foliage lasts poorly and the bracts lose their color.

Bracts: Usually 12 to 16 in number, in overlapping arrangement with a tight center which provides a full effect. Mature and over-ripe blooms develop increasing numbers of bracts, often as many as 25 to 30, which cascade in 2 or 3 layers thereby increasing the fullness of the bloom. Many of the bracts have a unique arched appearance.

*Size.*—Various, up to 6 inches long and 4 inches wide.

*Shape.*—Ovate, acuminate with substantially entire margins with some dentations. Small bracts are elliptic.

*Color.*—Bright red. Upper side — Between RHS 46A, 46B and 45A. Under side — Near RHS 45B.

*Ribs and veins.*—Light green color, appearing on the under side of the bracts.

*Retention.*—Long lasting, similar to that of the Annette Hegg varieties.

In general, this new poinsettia plant is distinctly different in appearance and is easily recognizable from other commonly marketed varieties. This is primarily due to its short growth, easy self-branching, uniquely arched shape, and the abundance of the bracts. Because of its easy branching habit of growth, the abundance of cuttings which it produces which root very quickly, and because of its early blooming at low temperature, it is a very profitable variety to utilize.

I claim:

1. A new and distinctive red poinsettia cultivar substantially as herein shown and described, characterized by its short and rapid habit of growth, its easy self-branching, the unique arched shape and abundance of the bracts, its easy branching habit, and its early blooming habit at low temperatures.

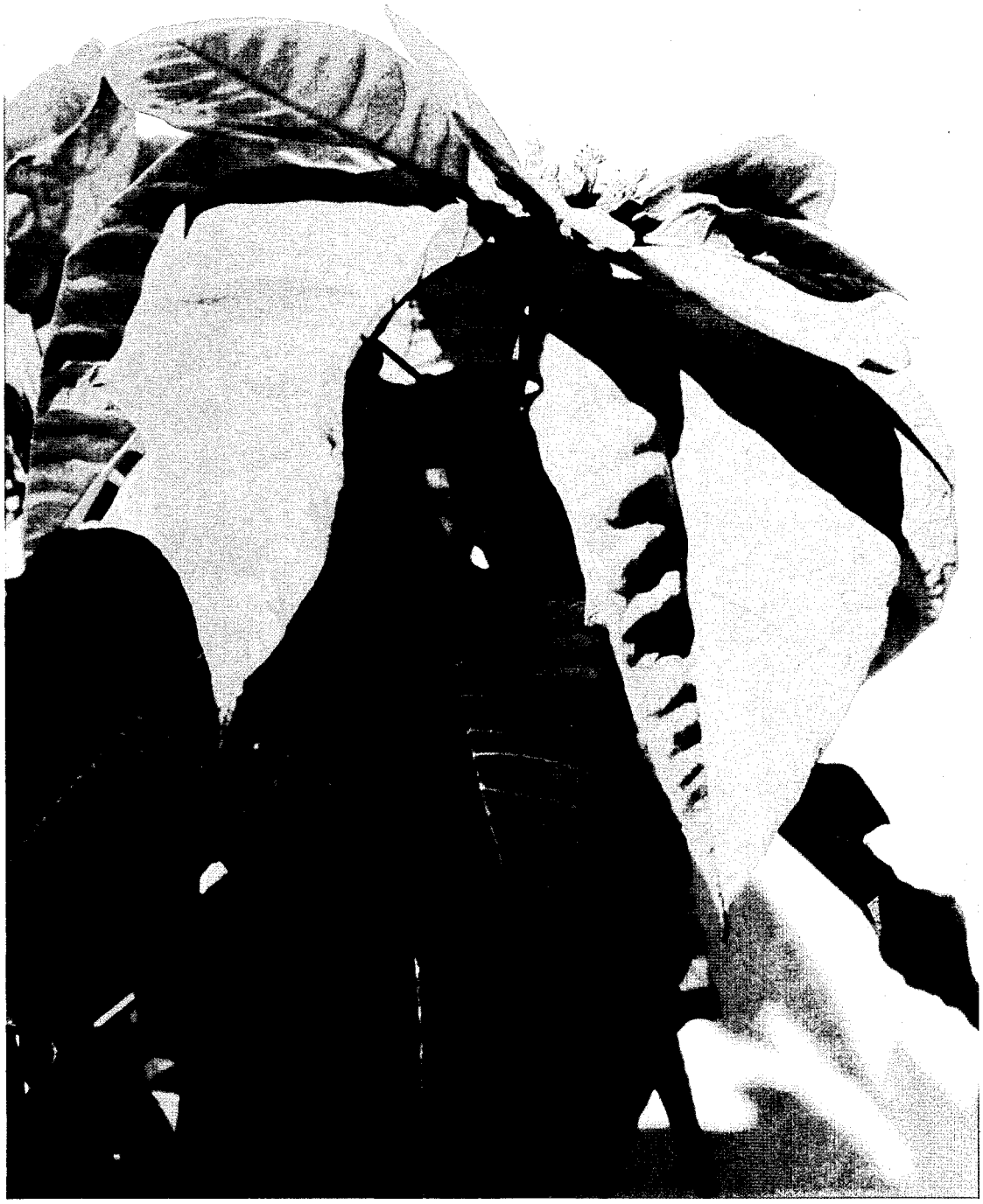

* * * * *